(12) United States Patent  (10) Patent No.: US 7,013,169 B2
Bowe  (45) Date of Patent: Mar. 14, 2006

(54) DUAL STEER PRESHAPED CATHETER

(75) Inventor: Wade Bowe, Temecula, CA (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 175 days.

(21) Appl. No.: 10/351,847

(22) Filed: Jan. 27, 2003

(65) Prior Publication Data

US 2004/0147827 A1   Jul. 29, 2004

(51) Int. Cl.
  *A61B 5/04*   (2006.01)
  *A61B 18/14*  (2006.01)
  *A61N 1/05*   (2006.01)
(52) U.S. Cl. .................. 600/374; 606/41; 607/122
(58) Field of Classification Search ............... 600/374; 606/41; 607/122
  See application file for complete search history.

(56) References Cited

U.S. PATENT DOCUMENTS

| 5,383,852 A | * | 1/1995 | Stevens-Wright | ........ 604/95.04 |
| 5,673,695 A | * | 10/1997 | McGee et al. | .............. 600/374 |
| 6,096,036 A | | 8/2000 | Bowe et al. | |
| 6,572,611 B1 | * | 6/2003 | Falwell | ........................ 606/41 |

\* cited by examiner

Primary Examiner—Lee S. Cohen
(74) Attorney, Agent, or Firm—Hollingsworth & Funk, LLC

(57) ABSTRACT

An electrophysiology catheter includes a flexible shaft with one or more electrodes disposed at a distal end having a preformed curve. A first steering apparatus allows altering a curvature of the distal end and a second steering apparatus allows steering of the distal end without significantly altering the curvature of the distal end. The first and second steering apparatuses are used for maneuvering the catheter and providing positive contact between the distal end and the tissue targeted for treatment.

21 Claims, 5 Drawing Sheets

DUAL STEER PRESHAPED CATHETER

FIELD OF THE INVENTION

The invention relates generally to catheter systems, and, more particularly, to pre-shaped electrophysiology catheters used for treating heart conditions.

BACKGROUND OF THE INVENTION

Electrophysiological (EP) treatments involve procedures for addressing cardiac arrhythmias and related heart diseases. In general, EP heart treatments involve introducing one or more electrodes into the heart where a diagnostic or therapeutic procedure can be carried out. The electrodes are oftentimes attached to the tip of an EP catheter. The EP catheter can be used for procedures such as mapping of electrical activity and ablation. Ablation procedures involve use of powerful electrodes to intentionally damage small areas of cardiac tissue that cause arrhythmia or other heart disorders.

Maneuvering EP catheters into heart chambers can be complicated. The path that must be traversed is often complex. The catheters must be sufficiently flexible to maneuver through convoluted geometries, yet stiff enough to facilitate pushing and torquing of the catheter from a proximal location.

Once an EP catheter is in the general location of therapy, a positive contact must be made between the catheter and target heart tissue. Oftentimes, the EP catheter includes a preshaped tip optimized for the intended cardiac structure. After positioning the catheter within the target area, the shape of the distal end region of an EP catheter may not always be ideally suited to the task. In such an event, the catheter must often be removed and a different shaped catheter introduced, thus adding excess time and complication to the cardiac mapping or ablation procedure.

There is a need for an EP catheter that provides for easy maneuvering and in-place alteration of the catheter's distal end region. The present invention addresses these needs, as well as other deficiencies of prior art implementations and techniques.

SUMMARY OF THE INVENTION

To overcome the limitations in the prior art described above, and to overcome other limitations that will become apparent upon reading and understanding the present specification, the present invention discloses a pre-shaped, steerable catheter that is particularly well suited for use in electrophysiological treatments involving chambers, vasculature, and other structures of the heart.

In one embodiment, an electrophysiology catheter system includes a flexible shaft having a preformed curve at a distal end. One or more electrodes are disposed along the distal end of the shaft. The shaft includes a shape deflection area defined as a region on the shaft between the preformed curve and a generally straight proximal portion of the shaft. A first anchor member is located at a distal portion of the preformed curve and a second anchor member is located distal to the shape deflection area of the flexible shaft.

First and second steering tendons are respectively coupled to the first and second anchor members. A force applied to a proximal end of the first steering tendon causes a change in the curvature of the preformed curve. A force applied to the proximal end of the second steering tendon causes a movement of the distal end of the flexible shaft relative to the proximal portion of the flexible shaft.

In another embodiment of the present invention, a method of providing electrophysiological therapy to cardiac tissue includes introducing a catheter adapted for electrophysiology into a heart chamber. The catheter is maneuvered so that a distal end of the catheter is proximate the heart tissue. A first steering apparatus of the catheter is activated to change a curvature of the distal end of the catheter. A second steering apparatus of the catheter is activated to change an orientation of the distal end relative to a proximal portion of the catheter. Actuating either of the first and second steering apparatuses causes the distal end of the catheter to conform to the contour of the subject heart tissue.

In another embodiment of the present invention, a catheter adapted for electrophysiological therapy includes a flexible shaft with a preformed curve at a distal end of the flexible shaft. An electrical energy delivery means is disposed along the distal end of the flexible shaft. The shaft includes a shape deflection area, defined as a region on the shaft between the preformed curve and a generally straight proximal portion of the flexible shaft.

A first steering means is included for changing a curvature of the preformed curve of the flexible shaft. A second steering means is included for changing a movement of the distal end of the flexible shaft about the shape deflection area without substantially changing the curvature of the preformed curve of the flexible shaft.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
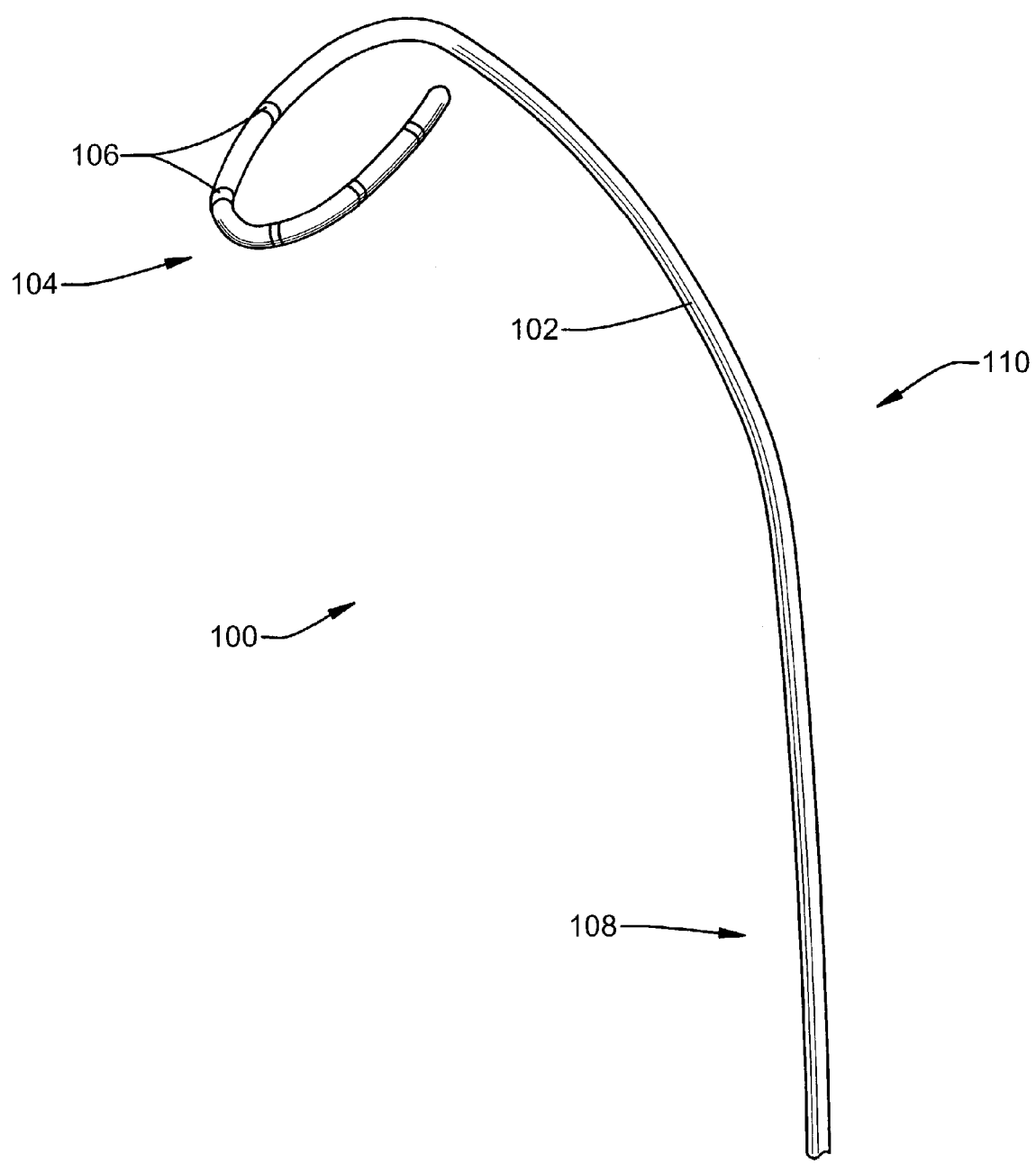
FIG. 1 is a perspective view of the distal end of a catheter according to an embodiment of the present invention.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

In broad and general terms, a catheter system of the present invention employs a flexible shaft having a preformed bend at a distal end. A plurality of electrodes are deployed along the outer surface of the catheter's distal end. Two steering tendons are deployed in the catheter. One steering tendon causes as change in the shape of the preformed distal bend, while the other steering tendon causes the distal section to move relative to the proximal portion of the catheter shaft.

A catheter according to the present invention may be adapted for electrophysiology (EP) treatments within the chambers of the heart. It is appreciated, however, that the concepts described herein are applicable to any type of catheter, such as guide catheters and drug delivery catheters. For purposes of illustration, the invention will be described in terms of an EP catheter used by a clinical electrophysiologist when mapping electrical paths and ablating heart tissues to eliminate arrhythmias, and specifically to treat atrial fibrillation.

EP catheters typically fall within two general categories: preshaped catheters and steerable catheters. The contours of preshaped catheters are generally fixed. This is often achieved in production by constraining the catheter's distal end within a shaping fixture and warming the fixture until the catheter assumes the intended shape (i.e., by "heat setting" the polymer shaft). A steerable catheter, in contrast, is generally formed to include a straight end, and a curve is induced by applying tension to one or more steering tendons typically connected to the distal tip of the catheter. When steered, the distal ends of such steerable catheters may assume a circular or semi-circular arc having a radius of curvature that depends on the amount of tension applied to the steering tendon(s).

In a catheter according to the present invention, the end of the catheter is preshaped to approximate the anatomical requirement. The catheter's pre-shaped portion is preferably set by inclusion of a preformed stylet, but may also be set by heat setting the shaft. Once the preformed portion of the catheter is within the heart chamber, the catheter's shape is adjustable at at least two points via at least two internal steering mechanisms. In this way, a catheter according to the present invention provides advantages of both preshaped and steerable catheters.

Turning now to FIG. 1, a distal portion of an EP catheter 100 is shown. The catheter 100 includes a flexible shaft 102 that is suited for maneuvering into anatomical locations such as heart vessels. The shaft 102 is typically formed of a polymeric material and can include reinforcing and stiffening features such as metallic sheathing or braiding.

A distal end 104 of the catheter 100 includes a preformed curve having a shape suitable for treating an area of interest. The distal end 104 illustrated in FIG. 1 is shown as a circular loop suited for ablation of certain blood vessels, such as the pulmonary vein. A closed or open loop at the distal end 104 has been found useful for ablation in veins and arteries, although it is appreciated that any curved shape can be imparted to the distal end 104 depending on the application and anatomical region targeted for treatment.

One or more electrodes 106 may be deployed on the distal end 104 of the catheter 100. Electrodes for ablation/EP can be formed as band electrodes for catheter mounting and are sometimes made from platinum/iridium. However, the electrodes 106 may be fabricated from any suitable materials, such as stainless steel for electrocardiogram measurements. Other measurement devices may also be employed on the distal end 104 with the electrodes 106. Devices such as thermal sensors (not shown) can be used when performing ablation to ensure lesions are effectively formed by the electrodes.

The curvature of the distal end 104 of the catheter 100 can be made variable by including various steering apparatuses (shown in later figures) within the flexible shaft 102. The flexible shaft 102 is generally straight at a proximal portion 108. Between the proximal portion 108 and the distal end 104 a predetermined deflection area 110 is defined. The distal end 104 can be made to deflect about the deflection area 110 by use of a second steering apparatus (shown in later figures).

In practice, the location of the deflection area 110 may vary slightly, given that bending may occur over differing portions of the shaft 102 under differing conditions (e.g., temperature, local support structures, multiple steering apparatus, etc.). Regardless, it is appreciated that a steering apparatus can be devised to restrict bending to a predictable deflection area 110 under most conditions. By deflecting the shaft 102 about the deflection area 110, the relative orientation of the distal end 104 can be varied without affecting the shape of the distal end 104.

Figure 2:
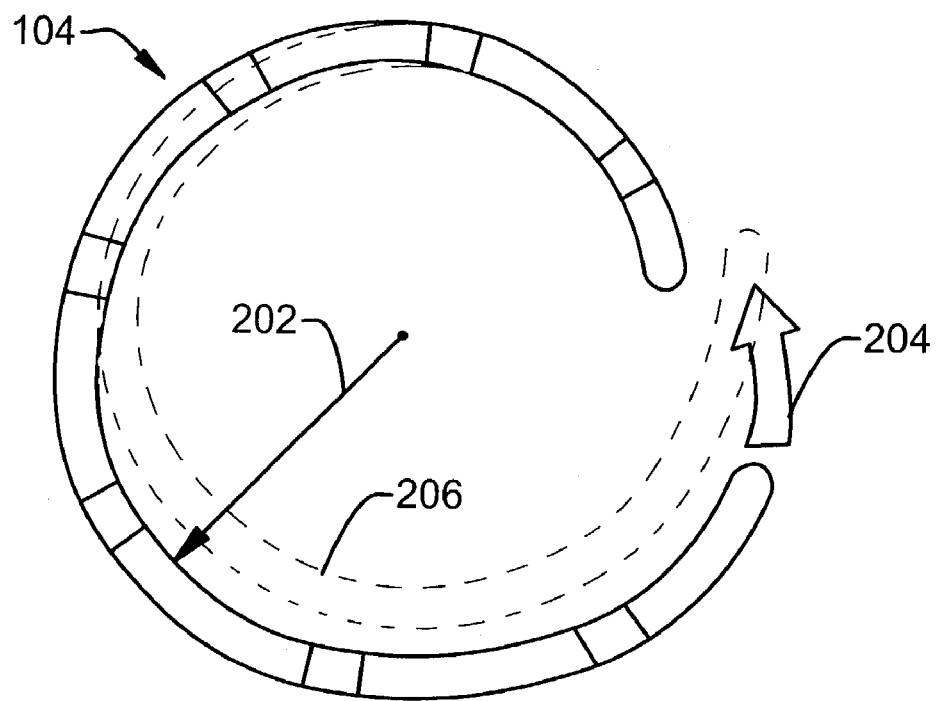
FIG. 2 is a top view of the distal end of the catheter showing a steering mode that changes a distal end curvature according to the concepts of the present invention.
Figure 3:
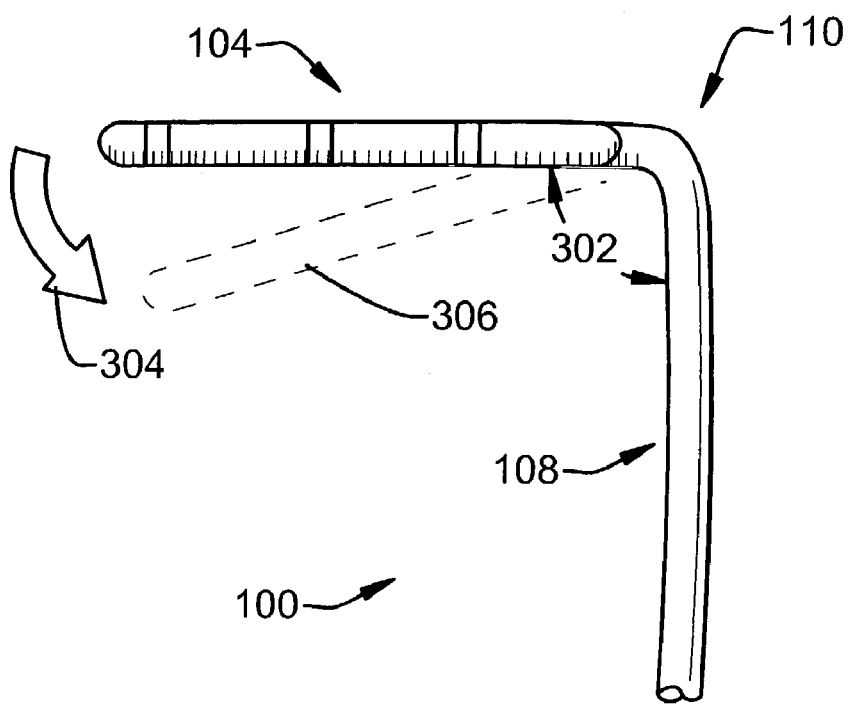
FIG. 3 is a side view of the distal end of the catheter showing an articulation mode of the catheter's distal end according to concepts of the present invention.

FIGS. 2 and 3 illustrate the deflection of the catheter's distal end 104 by use of steering apparatuses. FIG. 2 is a top view of the catheter 100 (the designation of a "top" view is arbitrary and assumes the proximal potion 108 of the shaft is oriented vertically as seen in FIG. 3). The distal end 104 has a radius of curvature 202 that can be increased or decreased by a steering apparatus. The arrow 204 indicates the general direction of movement near the distal tip when the radius of curvature 202 is decreased. When decreasing the radius of curvature 202, the distal end 104 assumes a deflected orientation 206 as shown in dashed lines. When a steering mechanism increases the radius of curvature 202, the opposite deflection is seen (i.e., the loop widens).

FIG. 3 is a side view of the catheter 100 in an orientation similar to that of FIG. 2. The distal end 104 forms an angle 302 with respect to the proximal portion 108 of the catheter 100. A steering apparatus can be used to rotate the distal end 104 about the deflection area 110, thereby increasing or decreasing the angle 302. Decreasing the angle 302 causes the distal end 104 to deflect in a direction generally indicated by the arrow 304. The deflected orientation 306 caused by decreasing the angle 302 is shown in dashed lines. Note that the curvature of the distal end 104 can remain substantially unchanged while changing the angle 302.

Figure 4:
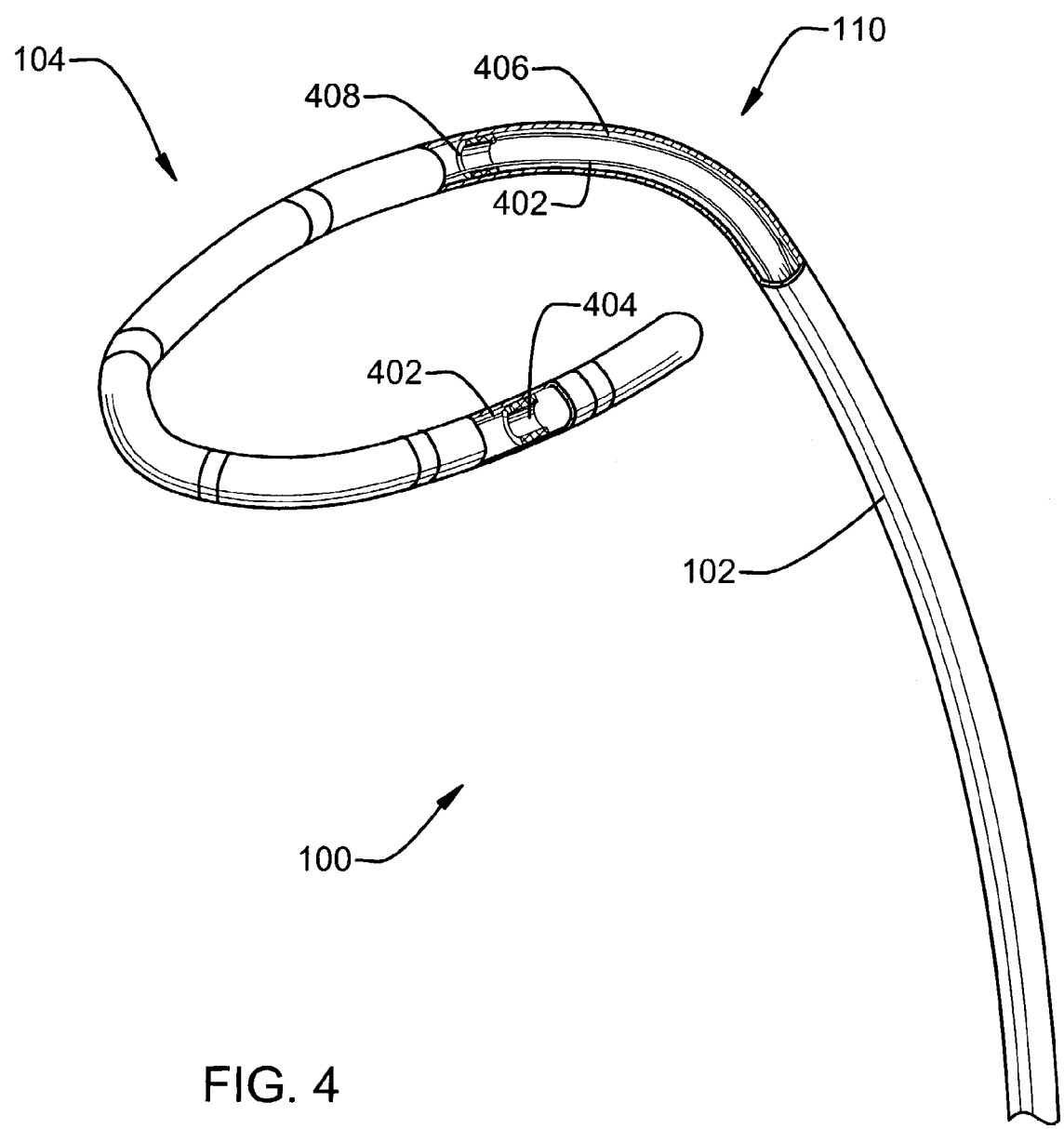
FIG. 4 is a perspective cutaway view of the distal end of the catheter showing steering tendons and anchor members according to an embodiment of the present invention.

Turning now to FIG. 4, an exemplary arrangement of a steering apparatus is shown. A first steering tendon 402 is attached to a first anchor member 404 located at a distal portion of the preformed distal end 104. A second steering tendon 406 is attached to a second anchor member 408 located distal to the deflection area 110.

The anchor members 404, 408 can be constructed using various materials and construction methods known in the art, including simply bonding a distal portion of the tendon to the shaft. In the illustrated configuration, the anchor members 404, 408 are formed of stainless steel rings to which steering tendons 402, 406, respectively, can welded or soldered. The steering tendons 402, 406 may also be attached to the anchor members 404, 408 using a mechanical interference fit such as a crimp or a stop member. The steering tendons 402, 406 are typically made of metallic (e.g., stainless steel) members such as solid wire, braided wire, or ribbon material. It is possible to form tendons 403, 406 from non-metallic members such as high strength composite members (e.g., Kevlar, carbon fiber).

The anchor members 404, 408 may be embedded within the walls of the shaft 102 during shaft construction. Alternatively, the anchor members 404, 408 may be adhered to the inner wall of the shaft 102 by adhesive bonding or hot melting the shaft material. Hot melting may be performed by heating the anchor members 404, 408 while in intimate contact with the inner walls of the shaft 102. Another method of attaching the anchor members 404, 408 involves butting the bands against a support structure, such as a reinforcement cage or braid, of the shaft 102.

Figure 5:
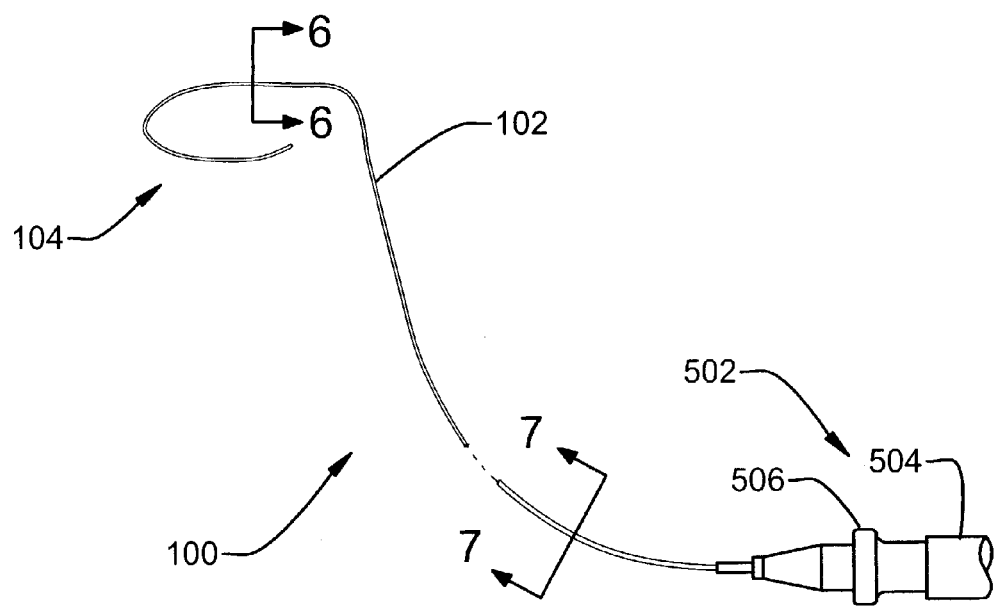
FIG. 5 is a side view of a catheter according to an embodiment of the present invention.
Figure 6:
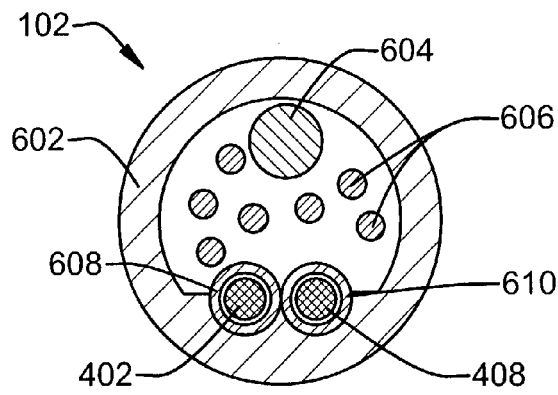
FIG. 6 is a cross sectional view of a distal portion the catheter shaft corresponding to section 6—6 in FIG. 5.
Figure 7:
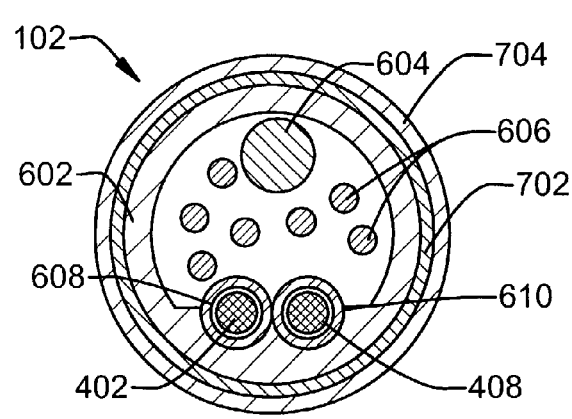
FIG. 7 is a cross sectional view of a proximal portion the catheter shaft corresponding to section 7—7 in FIG. 5.

FIGS. 5–7 illustrate further details of a catheter according to one embodiment of the present invention. FIG. 5 is an external view of the catheter 100 including a proximal handle assembly 502. The proximal handle assembly 502 typically includes a grip 504 and a steering member 506. The handle assembly 502 can be constructed by principles known in the art, such as described in U.S. Pat. Nos. 6,096,036 and 6,270,496, which are hereby incorporated by reference in their respective entireties.

FIG. 6 is a cross section of a distal portion of the catheter shaft 102 roughly corresponding to section 6—6 in FIG. 5. The shaft 102 includes a wall 602 formed of polymer, typically a high durometer Pebax material. For cardiac applications, the outer surface of the shaft wall 602 typically has an approximate outer diameter of 2.4 mm (7 F).

The shaft wall 602 encompasses a stylet 604. The stylet 604 is typically made of a resilient, shape-memory member such as a wire formed of nitinol wire or other superelastic alloy. A nitinol stylet 604 is preshaped by heating the stylet 604 while it is being constrained in the desired shape. A stylet 604 formed in this way is then inserted into the shaft 102 to impart the preformed shaped at the distal end 104 of the shaft 102. The stylet 604 is typically affixed at or near the tip of the shaft 102 to prevent migration of the stylet 604 within the catheter 100 during use.

The outer wall 602 of the shaft 102 also encompasses conductors 606 coupled to the tip electrodes 106 (see FIG. 1). The conductors 606 may provide power to the electrodes 106 in ablative applications, and/or provide signals from the electrodes 106 in EP mapping applications. Also shown within the shaft 102 are the steering tendons 402, 408. The steering tendons 402, 408 are disposed within lumens 608, 610, respectively. The lumens 608, 610 are typically formed of a lubricous material such as PTFE and may be affixed to an inner surface of the shaft wall 602.

FIG. 7 shows a cross section of a proximal portion of the catheter shaft 102. The layout of the shaft 102 is similar to that seen in FIG. 6, and additionally shows a reinforcing member 702 and an outer casing 704. The reinforcing member can include a braid, cage, ribbon, or other reinforcing member that provides axial and torsional stiffness to the shaft 102 while still allowing a reasonable amount of bending in the shaft 102. The outer casing 704 may be made of a Pebax material having a similar durometer as the shaft wall 602, or may be made of a different material having particular protective and/or lubricous properties.

The differences between the distal and proximal cross sections (e.g., inclusion of a proximal support member 702) as seen in FIGS. 6 and 7 result in the proximal portion having greater stiffness than the distal portion. Other variations in stiffness may also be advantageously induced along portions of the flexible shaft 102. To vary the stiffness of the shaft 102, for example, the bending properties of the shaft wall 602 may be changed (e.g., the durometer of the polymeric materials) or the stylet characteristics (e.g., outer diameter or cross section) can be varied along the shaft length. Varying the stiffness along the length of the shaft 102 can beneficially enhance the deflectability of the steered sections or to tune the stiffness of the distal end 104 to minimize the risk of trauma during use.

Figure 8:
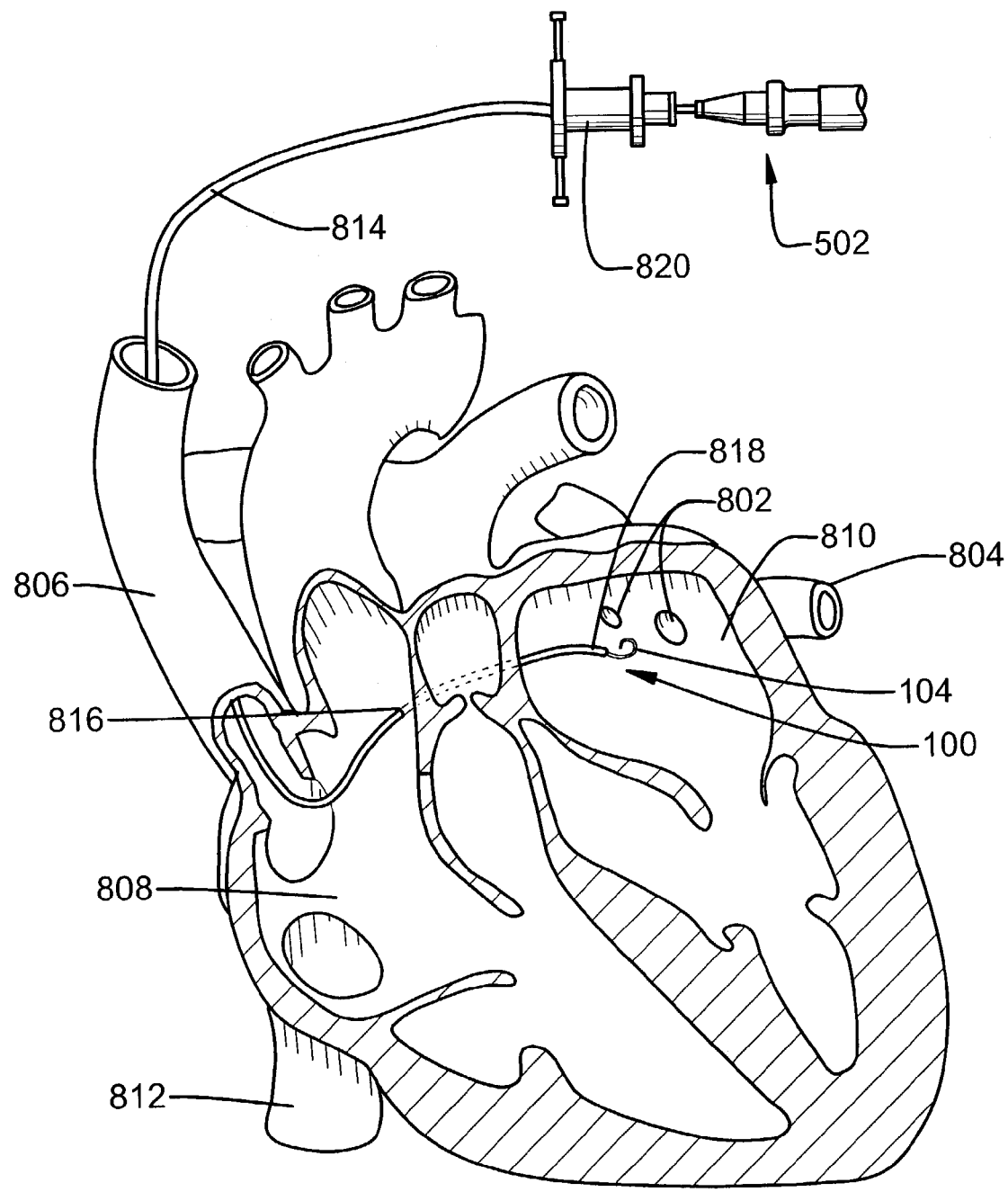
FIG. 8 is a cutaway view of a heart showing a catheter being used according to concepts of the present invention.

FIG. 8 illustrates one particular use of a catheter 100 according to concepts of the present invention. In this example, the catheter 100 is configured for EP mapping and/or ablation and is situated near the ostium(s) 802 of one or more pulmonary veins 804. The distal end 104 of the catheter 100 can be used to measure electrical impulses from heart tissue, as well as delivering electrical energy (ablation) to the treatment area of the heart. Ablation results in the production of a lesion that will block any impulses firing from around the treatment area.

As seen in FIG. 8, a distal end 104 shaped as a circular loop can be used to create circular continuous lesions for treatment of atrial fibrillation or atrial flutter. The ostiums 802 of the pulmonary veins 804 are common treatment areas for atrial fibrillation. Less common treatment areas include the superior vena cava 806, right atrium 808, left atrium 810, and the coronary sinus (not shown).

One procedure used in placing the catheter 100 into a heart chamber involves percutaneously introducing the catheter 100 through a large blood vessel. The catheter 100 is then guided through this vessel into the right atrium 808. Various routes to the right atrium can be used through upper blood vessels, such as the right internal jugular vein, and right or left subclavian vein. Lower blood vessels, such as the femoral veins, can also be used to enter the right atrium through the inferior vena cava 812.

A guide member 814 is typically introduced through one of these paths into the right atrium 808 and then to the left atrium 810 using a transseptal puncture 816. The guide member is typically an introducer sheath or guide catheter. In FIG. 8, an upper blood vessel route is illustrated, with the guide member 814 entering the right atrium 808 through the superior vena cava 806.

A guide member 814 typically includes a large lumen of sufficient size to allow the EP catheter 100 to pass through the lumen. A guide member 814 may include a catheter with steering features that allow maneuvering the catheter's distal end 818 from a proximal handle 820. Visualization techniques such as fluoroscopy or ultrasound may assist the clinician in moving the guide member 814 into the correct position.

Once the guide member 814 has cannulated the heart vessels of interest, the EP catheter 100 is advanced along the guide member 814. When the guide member 814 is configured as a catheter, the EP catheter is fed through a guide lumen of the guide catheter. The resilient distal end 104 of the EP catheter 100 will generally straighten out while being fed through a guide lumen. Once the tip of the EP catheter 100 emerges from the distal end 818 of the guide member 814, the distal end 104 of the EP catheter 100 will resume its preformed shape.

The first steering tendon 402 (see FIG. 4) allows adjustment of the curve at the EP catheter's distal end 104 to account for variability of heart structures such as the pulmonary vein ostium 802. Adjustment of the first steering tendon 402 allows the clinician to achieve positive contact between the distal end 104 and the ostium 802, thereby ensuring a more successful ablation.

The second steering tendon 406 (see FIG. 4) provides for varying the general orientation of the distal end 104 while maneuvering the catheter 100 to the destination vessels. The second steering tendon 406 thereby allows quicker positioning of the distal end 104 as well as allowing better electrode to tissue contact, especially when used in concert with the first steering tendon 402.

It is also appreciated that a steering feature on the guide member 814 (e.g., a steerable guide catheter) can further assist in positioning the distal end 104 of the EP catheter 100. The steering features of the EP catheter 100 and the guide member 814 in conjunction with visual feedback (e.g., fluoroscopy) allows a clinician to quickly and readily manipulate an EP catheter 100 into position.

Although a guide member 814 that includes a catheter or similar sheath apparatus is commonly used, it is appreciated that other guide members may be used in accordance with principles of the present invention. An EP catheter 100 may include an open lumen so that the catheter can be introduced over a guide wire or small catheter. Alternatively, the EP catheter 100 may be introduced without any guide apparatus.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A catheter adapted for electrophysiological therapy, comprising:
    a flexible shaft comprising:
        a preformed curve on a distal end of the flexible shaft;
        one or more electrodes disposed along the distal end of the flexible shaft; and
        a shape deflection area defined as a region on the flexible shaft between the preformed curve and a generally straight proximal portion of the flexible shaft;
    a first anchor member attached to a distal portion of the pre-formed curve; and
    a second anchor member attached to the flexible shaft distal to the shape deflection area of the flexible shaft;
    a first and second steering tendon coupled to the first and second anchor members, respectively, so that a force applied to a proximal end of the first steering tendon causes a change in a curvature of the preformed curve and a force applied to a proximal end of the second steering tendon causes movement of the distal end about the shape deflection area of the flexible shaft.

2. The catheter of claim 1, further comprising a stylet disposed within the distal end of the flexible shaft, the stylet substantially shaping the preformed curve on the flexible shaft.

3. The catheter of claim 2, wherein the stylet is a resilient and shape retentive member.

4. The catheter of claim 2, wherein the stylet comprises a nitinol wire.

5. The catheter of claim 1, wherein the preformed curve comprises a circular loop.

6. The catheter of claim 1, wherein the one or more electrodes comprise a plurality of band electrodes.

7. A catheter adapted for electrophysiological therapy, comprising:
    a flexible shaft comprising:
        a preformed curve on a distal end of the flexible shaft;
        an electrical energy delivery means disposed along the distal end of the flexible shaft; and
        a shape deflection area defined as a region on the shaft between the preformed curve and a generally straight proximal portion of the flexible shaft;
    a first steering means for changing a curvature of the preformed curve of the flexible shaft;
    a second steering means for changing an orientation of the distal end of the flexible shaft about the shape deflection area without substantially changing the curvature of the preformed curve of the flexible shaft.

8. The catheter of claim 7, further comprising a shape retentive means disposed within the distal end of the flexible shaft for shaping the preformed curve.

9. The catheter of claim 8, wherein the shape retentive means comprises a nitinol wire.

10. The catheter of claim 7, wherein the preformed curve comprises a circular loop.

11. The catheter of claim 7, wherein the electrical energy delivery means comprises one or more electrodes.

12. The catheter of claim 11, wherein the one or more electrodes comprise a plurality of band electrodes.

13. The catheter of claim 7, wherein the first steering means comprises a steering tendon attached to an anchor member at a distal portion of the pre-formed curve.

14. The catheter of claim 7, wherein the second steering means comprises a steering tendon attached to an anchor member distal to the shape deflection area of the flexible shaft.

15. A catheterization device adapted for electrophysiological therapy, comprising:
    means for introducing a catheter adapted for electrophysiology into a heart chamber;
    means for maneuvering the catheter so that a distal end of the catheter is proximate the heart tissue;
    means for actuating a first steering apparatus of the catheter to change a curvature of the distal end of the catheter; and
    means for actuating a second steering apparatus of the catheter to change an orientation of the distal end about a shape deflection area defined between the distal end curvature and a generally straight proximal portion of the catheter, without substantially changing the curvature of the distal end wherein actuating either of the first and second steering apparatuses causes the distal end of the catheter to conform to a contour of the heart tissue.

16. The device of claim 15, wherein the introducing means comprises means for guiding the catheter into the heart chamber.

17. The device of claim 16, wherein the guiding means comprises a distal end and means for steering the distal end of the guiding means.

18. The device of claim 15, further comprising means for delivering an electrical current to the heart tissue at the distal end of the catheter.

19. The device of claim 15, further comprising means for measuring an electrical signal from the heart tissue at the distal end of the catheter.

20. The device of claim 15, wherein the means for actuating the first steering apparatus of the catheter comprises means for applying a force to a first steering tendon of the catheter.

21. The device of claim 15, wherein the means for actuating the second steering apparatus of the catheter comprises means for applying a force to a second steering tendon of the catheter.

* * * * *